United States Patent
Pucci et al.

(10) Patent No.: US 11,718,582 B2
(45) Date of Patent: Aug. 8, 2023

(54) (R)-4-(1-(1-(4-(TRIFLUOROMETHYL)BENZYL)PYRROLIDINE-2-CARBOXAMIDE)CYCLOPROPYL)-BENZOIC ACID AS EP4 RECEPTOR ANTAGONIST

(71) Applicant: ROTTAPHARM BIOTECH S.R.L., Monza (IT)

(72) Inventors: Sabrina Pucci, Bernareggio (IT); Francesco Makovec, Monza (IT); Lucio Claudio Rovati, Monza (IT)

(73) Assignee: ROTTAPHARM BIOTECH S.R.L., Monza (IT)

(*) Notice: Subject to any disclaimer, the term of this patent is extended or adjusted under 35 U.S.C. 154(b) by 122 days.

(21) Appl. No.: 17/259,335

(22) PCT Filed: Jul. 4, 2019

(86) PCT No.: PCT/IB2019/055711
§ 371 (c)(1),
(2) Date: Jan. 11, 2021

(87) PCT Pub. No.: WO2020/012305
PCT Pub. Date: Jan. 16, 2020

(65) Prior Publication Data
US 2021/0130290 A1    May 6, 2021

(30) Foreign Application Priority Data
Jul. 12, 2018    (IT) .................. 102018000007134

(51) Int. Cl.
*C07D 207/16* (2006.01)
*A61K 31/401* (2006.01)
(Continued)

(52) U.S. Cl.
CPC .......... *C07D 207/16* (2013.01); *A61K 31/401* (2013.01); *A61P 19/02* (2018.01); *A61P 29/00* (2018.01)

(58) Field of Classification Search
CPC ........ C07D 207/16; A61P 19/02; A61P 29/00; A61P 15/02; A61P 27/02; A61P 35/00; A61K 31/401; A61K 31/402
(Continued)

(56) References Cited

FOREIGN PATENT DOCUMENTS

| WO | 2008104055 A1 | 9/2008 |
| WO | 2010121382 A1 | 10/2010 |

(Continued)

OTHER PUBLICATIONS

Berge et al, Pharmaceutical Salts, Journal of Pharmaceutical Science, Jan. 1977, p. 1-19. (Year: 1977).*
(Continued)

*Primary Examiner* — Taylor V Oh
(74) *Attorney, Agent, or Firm* — Troutman Pepper Hamilton Sanders LLP (Rochester)

(57) ABSTRACT

The following invention relates to (R)-4-(1-(1-(4-(trifluoromethyl)benzyl) pyrrodiline-2-carboxamide) cyclopropyl benzoic acid (Compound 1) or a salt thereof. Advantageous methods for obtaining the Compound 1 are also described, as well as pharmaceutical compositions containing it (R)-4-(1-(1-(4-(trifluoromethyl)benzyl)pyrrodiline-2-carboxamide) cyclopropyl benzoic acid (Compound 1) or a pharmaceutically acceptable salt thereof is described for use as an EP4 receptor antagonist in the treatment of a pathology that involves the activities of prostaglandin $E_2$ ($PGE_2$) in its pathogenesis.

18 Claims, 3 Drawing Sheets

(51) Int. Cl.
*A61P 19/02* (2006.01)
*A61P 29/00* (2006.01)

(58) Field of Classification Search
USPC .......................................................... 514/423
See application file for complete search history.

(56) References Cited

FOREIGN PATENT DOCUMENTS

WO 2012103071 A2 8/2012
WO 2013004290 A1 1/2013

OTHER PUBLICATIONS

International Preliminary Report on Patentability for PCT/IB2019/055711 (dated Jan. 12, 2021).
International Search Report and Written Opinion for PCT/IB2019/055711, dated Oct. 7, 2019.

* cited by examiner

(R)-4-(1-(1-(4-(TRIFLUOROMETHYL) BENZYL)PYRROLIDINE-2-CARBOXAMIDE)CYCLOPROPYL)-BENZOIC ACID AS EP4 RECEPTOR ANTAGONIST

This application is a national stage application under 35 U.S.C. § 371 of PCT Application No. PCT/IB2019/055711, filed Jul. 4, 2019, which claims the priority benefit of Italian Patent Application No. 102018000007134, filed Jul. 12, 2018, which are hereby incorporated by reference in their entirety.

FIELD OF THE INVENTION

The present invention describes a new derivative of D-proline, as a potent and selective antagonist of the EP4 receptor, the compound (R)-4-(1-(1-(4-(trifluoromethyl) benzyl) pyrrodiline-2-carboxamide) cyclopropyl benzoic acid (Compound 1) of formula Compound 1

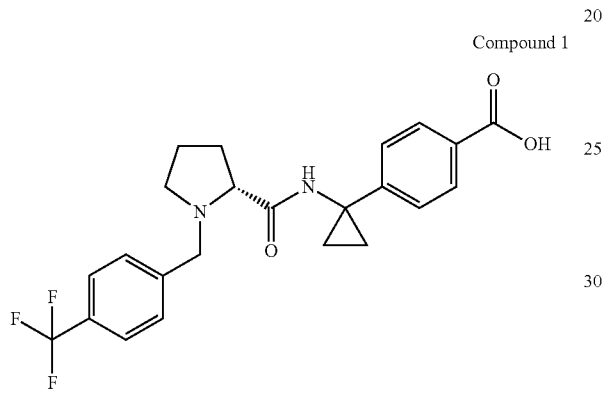

and the pharmaceutically acceptable salts thereof, processes for its preparation, the pharmaceutical compositions which comprise it and its use as a medicament for the treatment of diseases, in whose pathogenesis prostaglandin $E_2$ ($PGE_2$) plays a fundamental role, through its interaction with the EP4 receptor subtype.

Technical Field of the Invention

The EP4 receptor is of the 7-transmembrane receptor type, whose activation is normally associated with increased intracellular levels of cyclic adenosine monophosphate (cAMP).

Prostaglandin $E_2$ ($PGE_2$) acts through the activated EP4 receptor, as a cytokine amplifier system, for example interleukin-6 (IL-6), and induces the differentiation and expansion of pro-inflammatory T-helper lymphocytes (Th) (Yokoyama et al., Pharmacol. Rev. 2013; 65:1010-52).

WO 2013/004290 describes cyclic amino derivatives as EP4 receptor antagonists. In particular, in Example 7 it describes 4-(1-(6-(4-(trifluoromethyl) benzyl)-6-azaspiro [2.5] octan-5-carboxamide) cyclopropyl) benzoic acid (referred to as E7). E7, as enantiomer R briefly referred to as CR6086, showed high affinity and selectivity for the human EP4 receptor ($K_1$ 16.6 nM), functioning as a pure antagonist in the production of stimulated cAMP $PGE_2$. In experimental models of E7 cell cultures it inhibited the effects of important cytokines as mediators of rheumatoid arthritis: for example, it reduced the expression of IL-6 and of vascular endothelial growth factor (VEGF) in macrophages, the release of IL-23 in dendritic cells, the release of IL-17 in Th-17 lymphocytes. Moreover in models of collagen arthritis (CIA) in the rat and mouse, CR6086 has been shown to improve all parameters of induced arthritis: histopathology, inflammation, pain (Caselli et al., Arthritis Research & Therapy (2018)20:39).

However, CR6086 is obtained through a complex chemical synthesis shown below as Scheme 1:

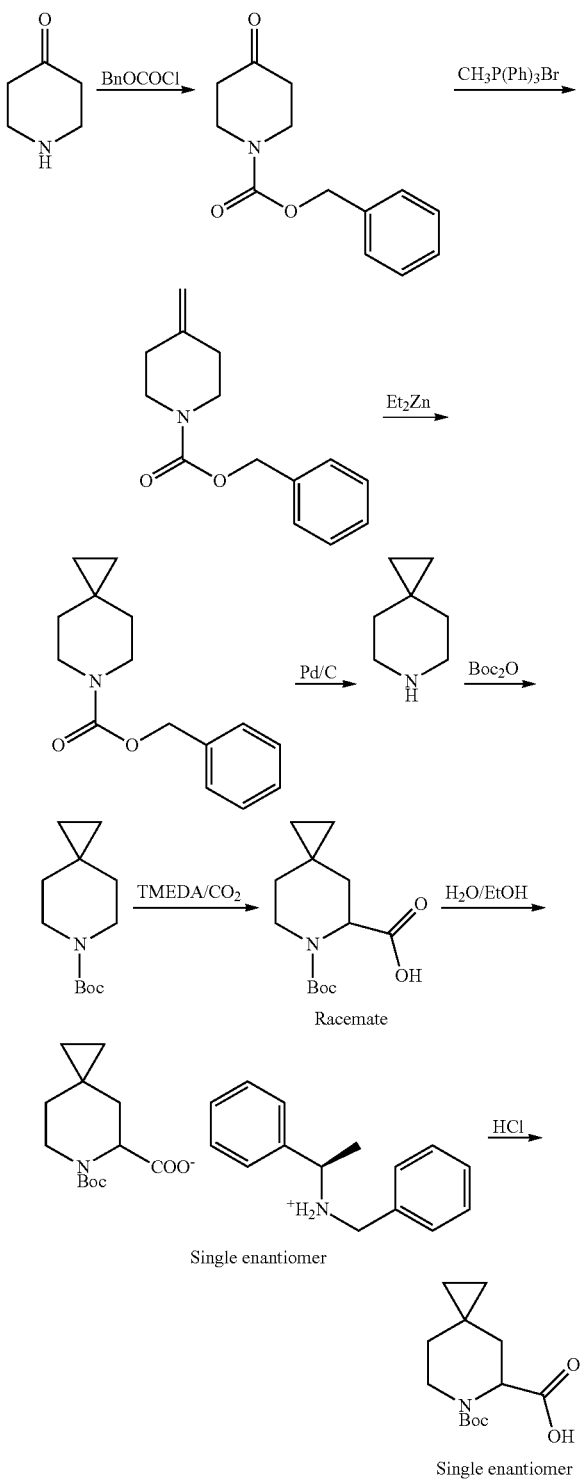

Analysing this synthesis described in WO2013/004290 and WO2011/006960, the complexity of the preparation of the synthesis intermediate CR6086, i.e. the following (R)-6-(tert-butoxycarbonyl)-6-azaspiro [2.5] octane-5-carboxylic acid is clearly shown:

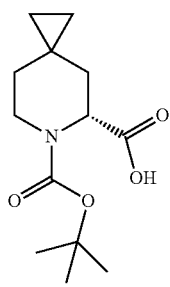 [SMILES: CC(C)(C)OC(=O)N1CCC2(CC2)C[C@@H]1C(=O)O]

As indicated in scheme 1 above, this synthesis consists in the sequence of 8 steps: After starting from the commercially available piperidin-4-one, the amino group is protected with benzyl chloroformate. The Wittig reaction takes place to convert the ketone in double bond under standard conditions. The double bond is converted into cyclopropyl using diethyl zinc and the protecting group on the amine is removed by hydrogenolysis. The amine is re-protected with tert-butyl carbonate anhydride and the intermediate obtained to give the acid as a racemate mixture is carbonated. The resolution of the racemate occurs by the selective precipitation of the single enantiomer as salt, using (R)—N-benzyl-1-phenylethane-1-amine. Finally, by acidifying the racemate salt solution with HCl, the intermediate (R)-6-(tert-butoxycarbonyl)-6-azaspiro[2.5]octano-5-carboxylic acid is obtained.

It is therefore felt the need for new analogous EP4 receptor inhibitors, but whose synthesis is less complicated.

A first object of the present invention is therefore to provide a new selective antagonist drug of the EP4 receptor for the pharmacological treatment of diseases requiring an antagonist of the aforementioned receptor, at least equal to CR6086, but which is at the same time obtainable with much less complex synthetic routes.

SUMMARY OF THE INVENTION

The objects indicated above were obtained by means of an original derivative of D-proline, that is (R)-4-(1-(1-(4-(trifluoromethyl)benzyl) pyrrodiline-2-carboxamide) cyclopropyl benzoic acid (Compound 1) having the following structure:

(Compound 1)

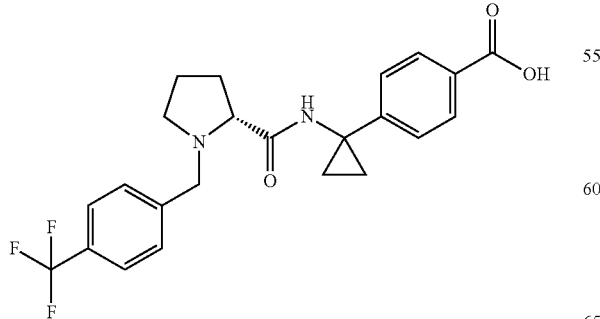

or a salt thereof.

The present invention therefore relates to Compound 1 which is a powerful antagonist of the EP4 receptor.

Furthermore, as will be apparent from the following description, the inventors have prepared the Compound 1 through two synthesis procedures which overcome the disadvantages of the prior processes for making CR6086.

Therefore, in a further aspect the invention relates to a process for the preparation of (R)-4-(1-(1-(4-(trifluoromethyl)benzyl) pyrrodiline-2-carboxamide) cyclopropyl benzoic acid (Compound 1) or a salt thereof which comprises the steps:

a) forming the amide (intermediate P1) by reacting (tert-butoxycarbonyl)-D-proline (N-Boc-D-proline) with methyl 4-(1-aminocyclopropyl) benzoate in the presence of a coupling agent

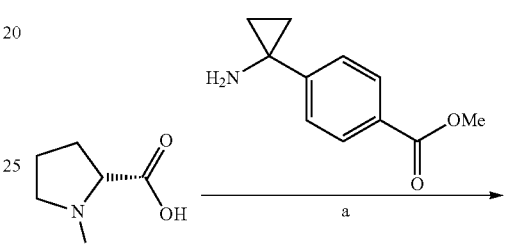

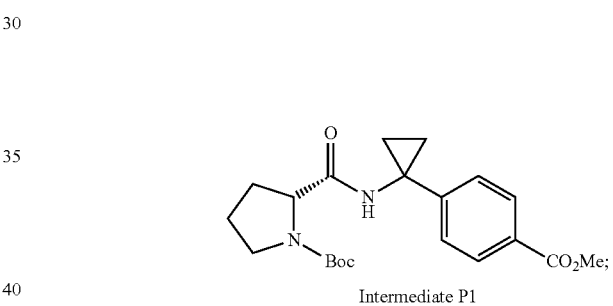

Intermediate P1 b) deprotecting the Boc group of the intermediate P1 with at least one acid in order to obtain the intermediate P2

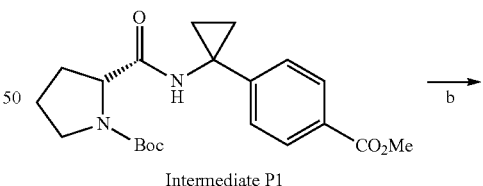

Intermediate P1

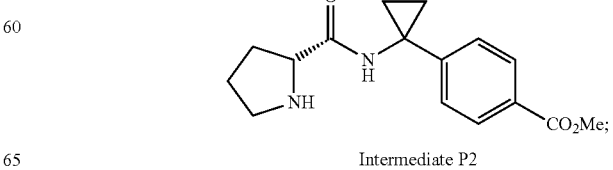

Intermediate P2 c) alkylating the intermediate P2 with 4-trifluoromethyl benzyl bromide in the presence of a base in order to obtain the methyl ester derivative (Intermediate P3)

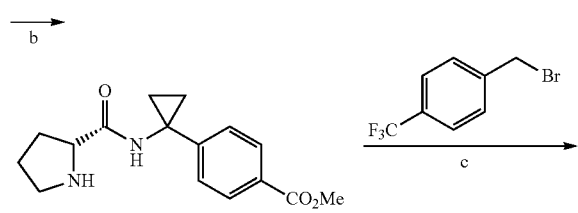

Intermediate P2

Intermediate P3 and
d) hydrolysing the derivated methyl ester (Intermediate P3) in the presence of a strong base in order to obtain the Compound 1

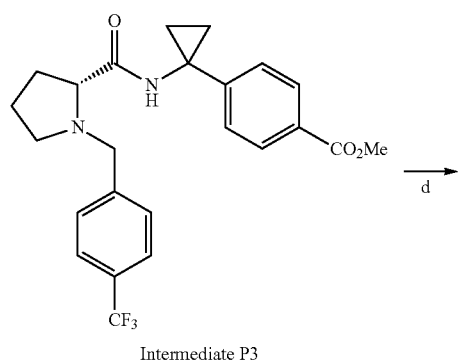

Intermediate P3

Compound 1

The process of the invention illustrated above resulted to be extremely advantageous both for the simplicity of its operative steps, and also for the use in step a) of N-Boc-D-proline, whose commercial cost is at least 20 times lower than that of the intermediate of the prior art, i.e. (R)-6-(tert-butoxycarbonyl)-6-azaspiro [2.5] octane-5-carboxylic acid used in the synthesis of CR6086.

In a further aspect the invention relates to another process for the preparation of (R)-4-(1-(1-(4-(trifluoromethyl)benzyl) pyrrodiline-2-carboxamide) cyclopropyl benzoic acid (Compound 1) or a salt thereof, which comprises the steps of:

a) alkylating D-Proline with 4-trifluoromethylbenzyl bromide in the presence of a strong base employing an alcohol as solvent in order to obtain the intermediate P4

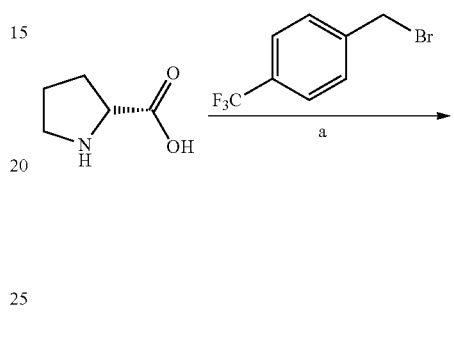

Intermediate P4 b) forming the amide (Intermediate P3) by reacting the intermediate P4 with methyl 4-(1-aminocyclopropyl) benzoate in the presence of a coupling agent

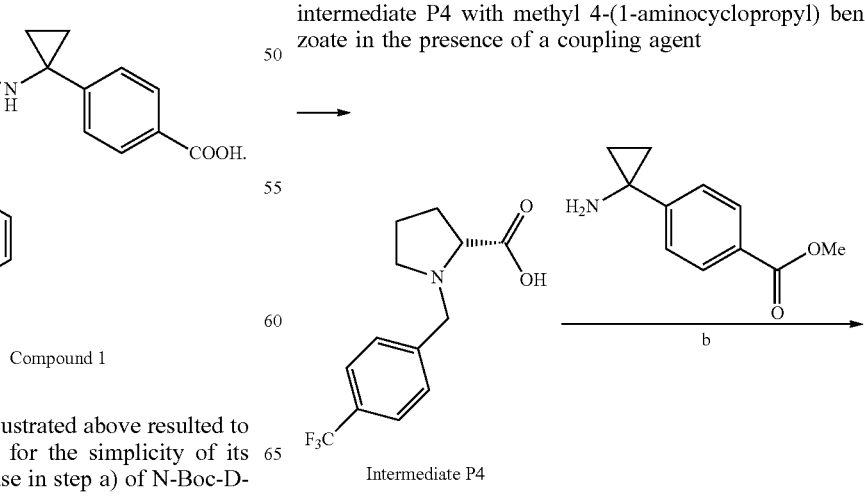

Intermediate P4

-continued

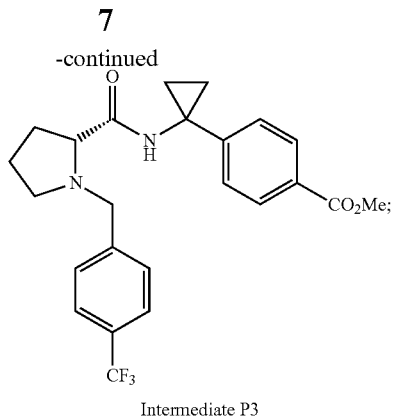

Intermediate P3 and
c) hydrolysing the Intermediate P3 in the presence of a strong base in order to obtain the Compound 1

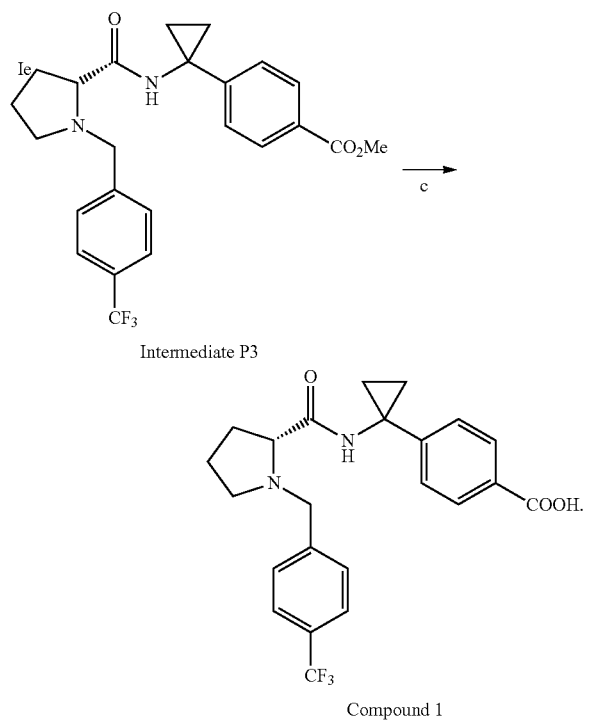

This process of preparing compound 1 or a pharmaceutically acceptable salt thereof which provides for the further reduction of a step for its synthesis, starting in this case with the direct alkylation of D-proline with 4-(trifluoromethyl) benzyl bromide, thereby avoiding the use of the protection and subsequent de-protection of N-Boc-D-proline, proved more advantageous from the synthesis point of view.

In a further aspect, the invention relates to the compound 1 or a pharmaceutically acceptable salt thereof for use as a medicament and pharmaceutical compositions comprising compound 1 or a pharmaceutically acceptable salt thereof of the invention and at least one pharmaceutically acceptable excipient.

In yet a further aspect the invention relates to compound 1 or a pharmaceutically acceptable salt thereof for use in the treatment of diseases, in whose pathogenesis prostaglandin $E_2$ (PGE2) plays a fundamental role through its interaction with the EP4 receptor subtype.

The invention therefore relates to compound 1 or a pharmaceutically acceptable salt thereof for use as a selective EP4 antagonist drug for the treatment of diseases in whose pathogenesis prostaglandin $E_2$ (PGE$_2$) plays a fundamental role.

The compound 1 of the invention has therefore proved to be able to inhibit the activities of prostaglandin $E_2$ (PGE$_2$) mediated by the EP4 receptor.

According to the present invention, therefore, compound 1 or a pharmaceutically acceptable salt thereof is a selective antagonist drug of the EP4 receptor for the treatment of a pathology selected from the group consisting of rheumatoid arthritis, spondyloarthritis (such as, for example, psoriatic arthritis and ankylosing spondylitis), arthrosis and pain, acute and chronic, due to inflammation such as osteoarthritis pain, or arthritis pain with an immunological aetiology such as rheumatoid arthritis.

In another aspect the invention relates to compound 1 or a pharmaceutically acceptable salt thereof for use as an antagonist drug of EP4 in tumour diseases. In this case the inventors assume that compound 1 can act in two distinct, alternative and concomitant ways: 1) the restoration of the immunological response against cancer cells, and 2) the inhibition of angiogenesis that nourishes the tumour tissue. In yet a further aspect, the invention relates to compound 1 or a pharmaceutically acceptable salt thereof as an antagonist drug of the EP4 receptor in the treatment of eye diseases. Among these it is possible to mention of retinopathy of prematurity (ROP), proliferative diabetic retinopathy and age-related macular degeneration (AMD) which have ocular neovascularization as a common pathological basis, largely linked to the activation of the EP4 receptor, and which are the leading cause of blindness in the developed world.

In yet a further aspect, the invention relates to compound 1 or a pharmaceutically acceptable salt thereof as an antagonist drug of the EP4 receptor in the treatment of endometriosis. In this case the compound is extremely advantageous, as endometriosis is a serious chronic disease that causes infertility and chronic pelvic pain in 10%-20% of women of reproductive age.

The invention will now be described in relation to the detailed description which follows and to the annexed figures.

BRIEF DESCRIPTION OF FIGURES

The characteristics and advantages of the present invention will become clear from the following detailed description, from the embodiments provided by way of illustrative and non-limiting examples and by the attached figures in which.

DETAILED DESCRIPTION OF THE INVENTION

Figure 1:
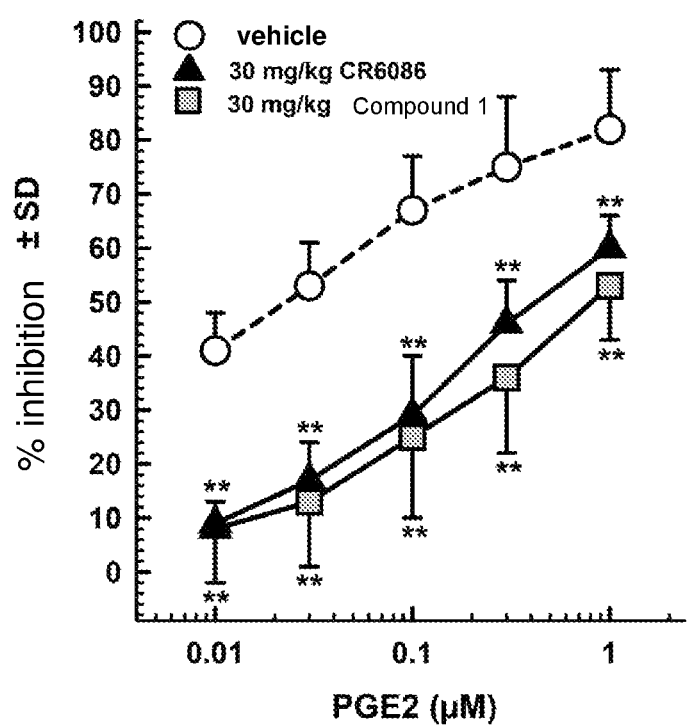
FIG. 1 represents the reversion of the effect of PGE$_2$ on the release of TNF alpha induced by LPS (sampling 1 hour after treatment) of example 9.

The invention therefore concerns (R)-4-(1-(1-(4-(trifluoromethyl)benzyl) pyrrodiline-2-carboxamide) cyclopropyl benzoic acid (Compound 1) having the following structure:

(Compound 1)

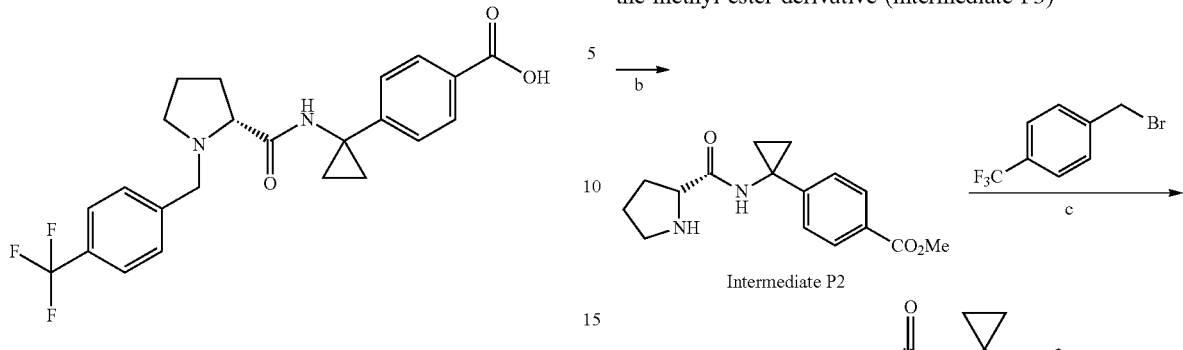

or a salt thereof.

The present invention therefore relates to Compound 1 which is a powerful antagonist of the EP4 receptor.

In a further aspect the invention relates to a process for the preparation of (R)-4-(1-(1-(4-(trifluoromethyl)benzyl) pyrrodiline-2-carboxamide) cyclopropyl benzoic acid (Compound 1) or a salt thereof, which comprises the steps:

a) forming the amide (intermediate P1) by reacting (tert-butoxycarbonyl)-D-proline (N-Boc-D-proline) with methyl 4-(1-aminocyclopropyl) in the presence of a coupling agent b) deprotecting the Boc group of the intermediate P1 with at least one acid in order to obtain the intermediate P2 c) alkylating the intermediate P2 with 4-trifluoromethyl benzyl bromide in the presence of a base in order to obtain the methyl ester derivative (intermediate P3)

and d) hydrolyzing the derivated methyl ester (Intermediate P3) in the presence of a strong base in order to obtain the Compound 1

Preferably in step a) the methyl 4-(1-aminocyclopropyl) benzoate is prepared as described in WO 2013/004290 and the coupling agent is preferably 1-ethyl-3-(3-dimethylaminopropyl) carbodiimide.

In particular, step a) provides for the formation of the amide between D-N-Boc proline, and methyl 4-(1-aminocyclopropyl) benzoate, in the presence of HOBt, EDCl and TEA for 24 hours; washing of the organic phase in sequence with a saturated solution of NaHCO₃, one of NH₄Cl and finally with water; anhydrification and evaporation of the solvent, purification of the product by silica gel chromatography, eluting with a cyclohexane/ethyl acetate gradient (100:0; 25/75). In step b) the at least one acid is preferably 2,2,2-trifluoroacetic acid.

In particular, step b) provides for the de-protection of the Boc group with trifluoroacetic acid and subsequent release of the salt on ion exchange resin.

In step c) the base is preferably cesium carbonate.

In particular, step c) involves the alkylation with 4-(trifluoromethyl) benzyl bromide in the presence of Cs₂CO₃ for 24 hours; subsequent washing with a 4.5% NaCl solution, solvent anhydrification and evaporation; purification of the residue, dissolved in DCM, by means of precipitation using n-heptane as a co-solvent; subsequent purification of the filtrate by flash chromatography on silica gel eluting with a DCM/ethyl acetate gradient (from 100/0 to 85/15).

In step d) the strong base is preferably sodium hydroxide. In step d) the strong base is preferably sodium hydroxide. Step d) preferably takes place in a water-miscible organic solvent mixture, more preferably the water-miscible organic solvent is tetrahydrofuran (THF). In particular, step d) provides for the hydrolysis of methyl ester in the presence of NaOH with subsequent purification by reverse phase chromatography eluting with only water and then methanol to give Compound 1 in the form of sodium salt.

As indicated, the process of the invention illustrated above resulted to be extremely advantageous not only for the simplicity of its operating steps, but also for the reagents used which are certainly low cost.

In a further aspect the invention relates to another process for the preparation of (R)-4-(1-(1-(4-(trifluoromethyl)benzyl) pyrrodiline-2-carboxamide) cyclopropyl benzoic acid (Compound 1) or a salt thereof, which comprises the steps of:

a) alkylating D-Proline with 4-trifluoromethylbenzyl bromide in the presence of a strong base employing an alcohol as solvent in order to obtain the intermediate P4 b) forming the amide (Intermediate P3) by reacting the intermediate P4 with methyl 4-(1-aminocyclopropyl) benzoate in the presence of a coupling agent

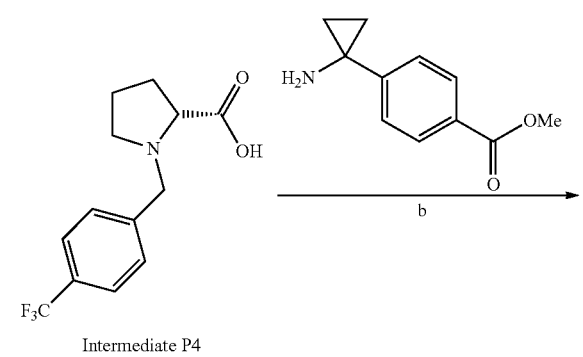

Intermediate P4

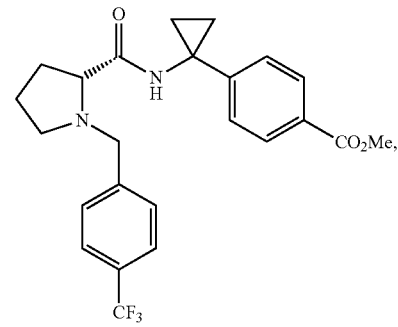

Intermediate P3 and c) hydrolysing the Intermediate P3 in the presence of a strong base in order to obtain the Compound 1

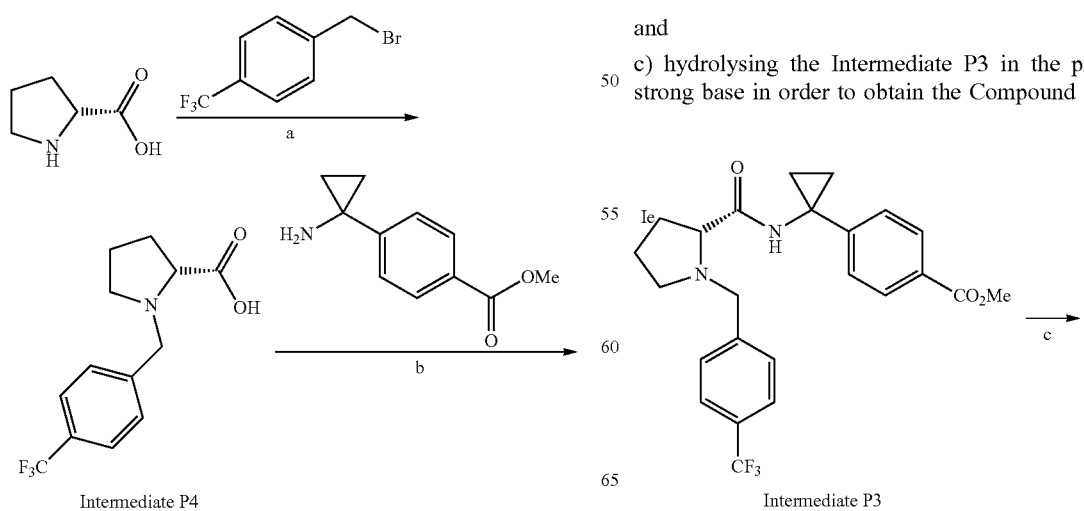

Intermediate P4

Intermediate P3

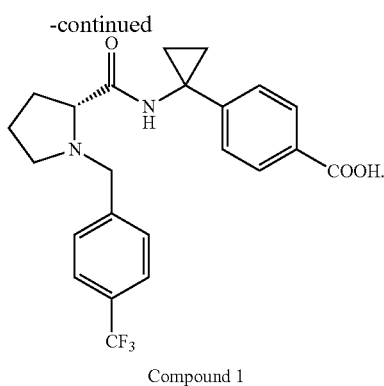

Compound 1

In step a) the base is preferably potassium hydroxide and the alcohol is 2-propanol. In particular, step a) consists in an alkylation of D-proline with 4-trifluoromethyl-benzyl-bromide in the presence of a strong base using an alcohol, preferably 2-propanol, as a solvent; product recovery by treatment with aqueous HCl and subsequent filtration and purification by treatment with acetone and tert-butyl-ether as a co-solvent.

In step b) the methyl 4-(1-aminocyclopropyl) benzoate is preferably prepared as described in WO 2013/004290 and the coupling agent is preferably 1-ethyl-3-(3-dimethylaminopropyl) carbodiimide.

In particular, step b) provides for the formation of the amide between 4-(trifluoromethyl) benzyl)-D-proline prepared according to the previous step a) and methyl 4-(1-aminocyclopropyl) benzoate hydrochloride, in the presence of hydroxybenzotriazole hydrate, TEA, EDCl dissolved in a DCM solution; washing of the organic phase with a saturated solution of NaHCO$_3$ and finally with water, anhydrification and evaporation of the solvent, purification and recovery of the methyl compound (R)-4-(1-(1-(4-(trifluoromethyl) benzyl) pyrrolidin-2-carboxamide) cyclopropyl) benzoate thus formed by treatment and precipitation with methyl-terbutyl ether.

In step c) the strong base is preferably sodium hydroxide. Step c) preferably takes place in a water-miscible organic solvent mixture, more preferably the water-miscible organic solvent is tetrahydrofuran (THF).

In step c) in particular, the methyl ester hydrolysis thus obtained according to what is described in the previous point b) and the recovery of the Compound 1 takes place successively according to what is described in point d) of the first process.

As indicated above this process of preparation of the compound which provides for the further reduction of a passage for its synthesis, starting in this case with the direct alkylation of D-proline with 4-(trifluoromethyl) benzyl bromide, thereby avoiding the use of the protection and subsequent de-protection of N-Boc-D-proline, proved to be more advantageous from the synthesis point of view.

In one advantageous aspect the compound 1 is in the form of salt, preferably a pharmaceutically acceptable salt, more preferably as hydrochloride salt or lithium salt or sodium salt.

In a further advantageous aspect, the compound 1 is in the form of a zwitterion.

In another aspect the invention relates to the compound 1 or a pharmaceutically acceptable salt thereof for use as a medicament and pharmaceutical compositions comprising compound 1 or a pharmaceutically acceptable salt thereof of the invention and at least one pharmaceutically acceptable excipient.

In yet a further aspect the invention relates to compound 1 or a pharmaceutically acceptable salt thereof for use in the treatment of diseases, in whose pathogenesis prostaglandin E$_2$ (PGE$_2$) plays a fundamental role through its interaction with the EP4 receptor subtype.

The invention therefore relates to compound 1 or a pharmaceutically acceptable salt thereof for use as a selective EP4 antagonist drug for the treatment of diseases in whose pathogenesis prostaglandin E$_2$ (PGE$_2$) plays a fundamental role.

According to the present invention, therefore, compound 1 or a pharmaceutically acceptable salt thereof is a selective antagonist drug of the EP4 receptor for the treatment of a pathology selected from the group consisting of rheumatoid arthritis, spondylarthritis (such as, for example, psoriatic arthritis and ankylosing spondylitis), arthrosis and pain, acute and chronic, due to inflammation such as osteoarthritis pain, or arthritis pain with an immunological aetiology such as rheumatoid arthritis. In another aspect the invention relates to compound 1 or a pharmaceutically acceptable salt thereof for use as an antagonist drug of EP4 in tumour diseases. In this case the inventors assume that compound 1 can act in two distinct, alternative and concomitant ways: 1) the restoration of the immunological response against cancer cells, and 2) the inhibition of angiogenesis that nourishes the tumour tissue. In yet a further aspect, the invention relates to compound 1 or a pharmaceutically acceptable salt thereof as an antagonist drug of the EP4 receptor in the treatment of eye diseases. Among these, mention can be made of retinopathy of prematurity (ROP), proliferative diabetic retinopathy and age-related macular degeneration (AMD) which have ocular neovascularization as a common pathological basis, largely linked to the activation of the EP4 receptor, and which are the leading cause of blindness in the developed world.

In yet a further aspect, the invention relates to compound 1 or a pharmaceutically acceptable salt thereof as an antagonist drug of the EP4 receptor in the treatment of endometriosis. In this case the compound is extremely advantageous, as endometriosis is a serious chronic disease that causes infertility and chronic pelvic pain in 10%-20% of women of reproductive age.

Further examples of embodiments of the present invention are given below by way of non-limiting example.

EXAMPLES

The reagents used in the following examples were purchased from various suppliers and used without further purification. The solvents were used in anhydrous form. The reactions in anhydrous environment were performed under a positive pressure of N$_2$.

The Proton Nuclear Magnetic Resonance spectra (1 H NMR) were recorded on the instrument Bruker Avance 400 MHz. The chemical shifts are reported in ppm (δ) using the residual solvent line as an internal standard. The multiplicity of signs is designated as: s, singlet; d, doublet; t, triplet; q, quartet; m, multiplet; br, enlarged sign.

The UPLC-Massa spectra were performed on the instrument Waters Acquity UPLC-SOD using a C18 column of Acquity UPLC-BEH (1.7 µM, 50×2.1 mm).

The flash chromatography on silica gel was performed on Biotage automatic flash chromatography systems (Sp1 and Isolera systems) using SNAP HP Biotage silica cartridges.

The reverse phase chromatography was performed on Biotage (Isolera) automatic flash chromatography systems using RediSep Gold C-18Aq cartridges. SPE-SCX cartridges are ion-exchange columns for solid phase extraction.

The rotatory power was measured with an Autopol V polarimeter (Rudolph Sci.) The following abbreviations are used here:

NH4Cl: ammonium chloride; NaHCO$_3$: sodium bicarbonate; Cs$_2$CO$_3$ cesium carbonate; NaOH: sodium hydroxide; KOH: potassium hydroxide; TEA: triethylamine; NH3: ammonia; HCl: hydrochloric acid; EDC: 1-ethyl-3-(3-dimethylaminopropyl) carbodiimide; Na$_2$SO$_4$: sodium sulphate; DCM: dichloromethane; EtOH: ethanol; MeOH: methanol; IsOH: 2-propanol; THF: tetrahydrofuran; t.a.: room temperature.

Example 1

Preparation of Compound 1 Through the First Process of the Invention

Preparation 1: Preparation of Tert-butyl (R)-2-((1-(4-(methoxy carbonyl) phenyl) cyclopropyl) carbamoyl) pyrrolidin-1-carboxylate (Intermediate P1)

N-hydroxybenzotriazole hydrate (25.6 g, 167 mmol) and EDC (40.1 g, 209 mmol) were added to a solution of (tert-butoxy carbonyl)-D-proline (30 g, 139 mmol) in DCM (550 ml) and the mixture was stirred for one hour at room temperature. After this time, methyl 4-(1-aminocyclopropyl) benzoate hydrochloride (33.0 g, 145 mmol) and TEA (26.2 ml, 188 mmol) were added. The reaction was stirred for 24 hours. When the reaction was complete, water (350 mL) was added and the two phases were stirred for about 10 minutes. The organic phase was separated from the aqueous phase and washed sequentially with a saturated solution of NaHCO$_3$ (300 ml), one of NH$_4$Cl (300 ml) and finally with 300 mL of water.

The organic phase was dried with Na$_2$SO$_4$ and concentrated to obtain a light yellowish solid whose purification by flash chromatography on silica gel, with a cyclohexane/ethyl acetate gradient (100:0; 25/75), provided the desired compound (49.5 g; yield 88%). (Intermediate P1).

MS: (ES/+) m/z: 389 [MH$^+$]
$^1$H NMR (400 MHz, CHLOROFORM-d) δ ppm: 7.94 (2H, d, J=8.31 Hz), 7.73 (1H, br. s.), 7.23 (2H, d, J=7.83 Hz), 4.29 (1H, br. s.), 3.91 (3H, s), 3.45 (2H, br. s.), 1.77-2.53 (4H, m), 1.47 (9H, br. s), 1.29-1.42 (4H, m):

Preparation 2: Preparation of Methyl (R)-4-(1-(pyrrolidin-2-carboxamide) cyclopropyl) benzoate (Intermediate P2)

Tert-butyl (R)-2-((1-(4-(methoxycarbonyl) phenyl) cyclopropyl) carbamoyl) pyrrolidin-1-carboxylate (49.5 g, 122 mmol) was dissolved in DCM (400 mL) and the mixture was cooled to 0° C. before adding 2,2,2-trifluoroacetic acid (80 mL, 1038 mmol). The reaction was left to reach to room temperature and then stirred for 3 hours. The solvents were evaporated and the crude residue loaded onto a SPE-SCX cartridge (150 g) eluting first with only MeOH and then with NH$_3$ 1M in MeOH. The fractions containing ammonia were evaporated to obtain the desired residual solid (30.9 g: yield 88%). (Intermediate P2).

MS: (ES/+) m/z: 289
$^1$H NMR (400 MHz, DMSO-d6) δ ppm 8.62 (1H, s), 7.80-7.91 (2H, m), 7.17-7.27 (2H, m), 3.83 (3H, s), 3.49-3.58 (1H, m), 2.77-2.92 (3H, m), 1.91-2.03 (1H, m), 1.56-1.74 (3H, m), 1.17-1.34 (4H, m).

Preparation 3: Preparation of methyl (R)-4-(1-(1-(4-trifluoromethyl) benzyl) pyrrolidin-2-carboxamide) cyclopropyl) benzoate (Intermediate P3)

Methyl (R)-4-(1-(pyrrolidin-2-carboxamide) cyclopropyl) benzoate (29.6 g, 103 mmol) was dissolved in THF (500 ml). Cs$_2$CO$_3$ (57.2 g, 176 mmol) and 4-(trifluoromethyl) benzyl bromide (16.82 ml, 109 mmol) were added in sequence and the mixture was stirred for 24 hours at room temperature. The THF was evaporated and the residue partitioned between DCM (250 ml) and water (250 ml) and the resulting mixture was stirred vigorously for about 10 minutes. The organic phase was separated from the aqueous phase and washed twice with a solution of 4.5% NaCl (250 ml), dried over Na$_2$SO$_4$ and concentrated to obtain a white solid (46.5 g), which was additioned with DCM (100 mL) and heated to about 40° C. until complete dissolution. At this point the solution was left to reach room temperature before adding n-Heptane (500 mL) to obtain a white precipitate which was then filtered and dried at 50° C. for 24 hours to obtain the desired compound (50 g; yield: 89%). (Intermediate P3).

MS: (ES/+) m/z: 447
$^1$H NMR (400 MHz, DMSO-d6) δ ppm 8.47 (1H, s), 7.77-7.85 (2H, m), 7.66-7.71 (2H, m), 7.58-7.65 (2H, m), 7.14 (2H, d, J=8.31 Hz), 3.78-3.90 (4H, m), 3.66 (1H, d, J=13.20 Hz), 3.11 (1H, dd, J=9.05, 4.65 Hz), 2.98-3.05 (1H, m), 2.34-2.42 (1H, m), 2.05-2.20 (1H, m), 1.70-1.87 (3H, m), 1.15-1.32 (2H, m), 0.98-1.15 (2H, m).

Preparation 4: Preparation of the sodium salt of (R)-4-(1-(1-(4-(trifluoromethyl) benzyl) pyrrolidin-2-carboxamide) cyclopropyl) benzoic acid (Compound 1)

Methyl (R)-4-(1-(1-(4-(trifluoromethyl) benzyl) pyrrolidin-2-carboxamide) cyclopropyl)-benzoate (40.95 g, 92 mmol) (Intermediate P3) was dissolved in a mixture of THF (450 ml) and water (250 ml) before adding NaOH (4.40 g, 110 mmol). The whitish suspension was stirred at room temperature for 24 hours. The organic solvent was evaporated and the residue loaded onto a RediSep Gold C-18Aq column eluted first with only water (2 column volumes) and finally with MeOH (3 column volumes). The fractions containing MeOH were concentrated and the resulting residue solid was dried at 60° C. under vacuum to give 35.5 g of Compound 1 sodium salt (84% yield).

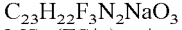
MS: (ES/+) m/z: 433 [MH$^-$]
$^1$H NMR (400 MHz, DMSO-d6) δ ppm 8.38 (1H, s), 7.65-7.77 (4H, m), 7.56-7.64 (2H, m), 6.87-7.01 (2H, m), 3.86 (1H, d, J=13.20 Hz), 3.64 (1H, d, J=13.69 Hz), 3.09 (1H, dd, J=9.05, 4.65 Hz), 2.94-3.04 (1H, m), 2.29-2.41 (1H, m), 2.03-2.19 (1H, m), 1.69-1.86 (3H, m).

Specific rotatory power: (α) D20, 1% in H$_2$O=30.2°.

Example 2

Preparation of Compound 1 Through the Second Process of the Invention

Preparation 1: Preparation of (4-(trifluoromethyl) benzyl)-D-proline (Intermediate P4)

50 g (0.43 moles) of D-proline were added to a solution of 73 g (1.3 moles) of potassium hydroxide dissolved in 500 ml of 2-propanol, and subsequently, in portions, 74 ml of 4-(trifluoromethyl) benzyl bromide (0.477 moles) dissolved in 300 ml of 2-propanol; the solution was reacted with stirring at 50° C. for 12 hours. The solution was subsequently cooled to 0° C. and the pH adjusted to about 4±1 with aqueous 32% HCl. The precipitated solid formed was filtered, washed with a little 2-propanol, dissolved in acetone, filtered hot and re-precipitated by adding methyl-terbutyl ether to obtain the desired compound (99 g; 83% yield) after filtration and drying. (Intermediate P4).

MS: (ES/+) m/z: 274

$^1$H NMR (400 MHz, DMSO-d6) δ ppm 11.66 (vbs), 7.69 (2H, d), 7.59 (2H, d), 4.07 (1H, d), 3.68 (1H, d), 3.25-3.32 (1H, m), 2.93 (1H, ddd), 2.39-2.48 (1H, m), 2.10 (1H, dq), 1.67-1.92 (3H, m)

Preparation 2: Preparation of methyl (R)-4-(1-(1-(4-(trifluoromethyl) benzyl) pyrrolidin-2-carboxamide) cyclopropyl) benzoate (Intermediate P3)

To a solution of 26 g (95.4 mmol) of 4-(trifluoromethyl) benzyl)-D-proline and N-hydroxybenzotriazole hydrate (17.6 g, 114 mmol) dissolved in 600 ml of DCM, 80 ml of TEA (570 mmol) and 20 g (105 mmol) of EDCl were added under nitrogen stream. The reaction mixture was left under stirring for about 6 hours, then 24 g (105 mmol) of methyl-4-(1-aminocyclopropyl) benzoate hydrochloride were added and then left to react always under stirring for a further 24 hours at room temperature. When the reaction was complete, water (500 mL) was added and the two phases stirred for about 10 minutes. The organic phase was separated from the aqueous phase and washed sequentially with a saturated solution of NaHCO$_3$ (400 ml), and finally with 400 mL of water. The organic phase was dried with Na$_2$SO$_4$ and concentrated to obtain a solid cream colour. This solid was suspended in 1 liter of methyl-terbutyl-ether, heated to boiling, filtered hot and the clear solution thus obtained was concentrated under vacuum to dryness to obtain a white solid which was then dried at 50° C. for 24 hours to obtain the desired compound (32.5 g; yield: 75%). (Intermediate P3).

MS: (ES/+) m/z: 447

$^1$H NMR (400 MHz, CHLOROFORM-d) δ ppm 7.80-8.01 (3H, m), 7.62 (2H, d), 7.41 (2H, d), 7.12-7.24 (2H, m), 3.86 (4H, s), 3.66 (1H, d), 3.27 (1H, dd), 3.07-3.18 (1H, m), 2.46 (1H, td), 2.21-2.38 (1H, m), 1.70-2.03 (3H, m), 1.05-1.44 (4H, m)

Preparation 3: Preparation of the sodium salt of (R)-4-(1-(1-(4-(trifluoromethyl) benzyl) pyrrolidin-2-carboxamide) cyclopropyl) benzoic acid (Compound 1)

Methyl (R)-4-(1-(1-(4-(trifluoromethyl) benzyl) pyrrolidin-2-carboxamide) cyclopropyl)-benzoate (40.95 g, 92 mmol) (Intermediate P3) was dissolved in a mixture of THF (450 ml) and water (250 ml) before adding NaOH (4.40 g, 110 mmol). The whitish suspension was stirred at room temperature for 24 hours. The organic solvent was evaporated and the residue loaded onto a RediSep Gold C-18Aq column eluted first with only water (2 column volumes) and finally with MeOH (3 column volumes). The fractions containing MeOH were concentrated and the resulting residue solid was dried at 60° C. under vacuum to obtain 35.5 g of Compound 1 sodium salt (84% yield).

$C_{23}H_{22}F_3N_2NaO_3$

MS: (ES/+) m/z: 433 [MH$^-$]

$^1$H NMR (400 MHz, DMSO-d6) δ ppm 8.38 (1H, s), 7.65-7.77 (4H, m), 7.56-7.64 (2H, m), 6.87-7.01 (2H, m), 3.86 (1H, d, J=13.20 Hz), 3.64 (1H, d, J=13.69 Hz), 3.09 (1H, dd, J=9.05, 4.65 Hz), 2.94-3.04 (1H, m), 2.29-2.41 (1H, m), 2.03-2.19 (1H, m), 1.69-1.86 (3H, m).

Specific rotatory power: (a)D20, 1% in H$_2$O=30.2°.

Example 3

Preparation of (R)-4-(1-(1-(4-(trifluoromethyl) benzyl) pyrrolidin-2-carboxamide) cyclopropyl) benzoic acid (Compound 1 Zwitterion)

1.7 ml (29.4 mmol) of acetic acid were added to a solution of 6.1 g (13.4 mmol) of the sodium salt of (R)-4-(1-(1-(4-(trifluoromethyl) benzyl) pyrrolidin-2-carboxamide) cyclopropyl) benzoic acid dissolved in 80 ml of H$_2$O and this solution was extracted twice with 80 ml of DCM. The combined organic phases were washed with H$_2$O and then dried on Na$_2$SO$_4$ and concentrated under vacuum to obtain a pale cream-coloured solid with an amorphous appearance (5.7 g; yield 96%).

$C_{23}H_{23}F_3N_2O_3$.

MS: (ES/+) m/z: 433

$^1$H NMR (400 MHz, DMSO-d6) δ ppm 12.68 (1H, br. s.), 8.45 (1H, s), 7.76-7.83 (2H, m), 7.65-7.72 (2H, m), 7.58-7.65 (2H, m), 7.08-7.17 (2H, m), 3.86 (1H, d, J=13.69 Hz), 3.66 (1H, d, J=13.20 Hz), 3.12 (1H, dd, J=9.29, 4.40 Hz), 2.97-3.06 (1H, m), 2.34-2.43 (1H, m), 2.05-2.19 (1H, m), 1.71-1.86 (3H, m), 1.15-1.30 (2H, m), 0.97-1.14 (2H, m)

Specific rotatory power: (a)D20, 1% in methanol=28.9°.

Example 4

Preparation of (R)-4-(1-(1-(4-(trifluoromethyl) benzyl) pyrrolidin-2-carboxamide) cyclopropyl) benzoic acid (Compound 1 HCl)

HCl 1 N (30 mL, 30 mmol) was added to a solution of 7 g (16.2 mmol) of (R)-4-(1-(1-(4-(trifluoromethyl) benzyl) pyrrolidin-2-carboxamide) cyclopropyl) benzoic acid (Compound 1 "zwitterion") dissolved in 300 ml of butan-2-one. The reaction mixture was stirred for 12 hours and the white precipitate formed in suspension was filtered and dried at 60° C. under vacuum to obtain 5.8 g of Compound 1 hydrochloride (yield 85%).

$C_{23}H_{23}F_3N_2O_3$ *HCl.

MS: (ES/+) m/z: 433

$^1$H NMR (400 MHz, METHANOL-d4) δ ppm 7.89-7.97 (2H, m), 7.70-7.83 (4H, m), 7.18 (2H, d, J=8.31 Hz), 4.45-4.60 (2H, m), 4.28 (1H, dd, J=9.05, 6.60 Hz), 3.68-3.79 (1H, m), 3.39-3.49 (1H, m), 2.61-2.75 (1H, m), 2.22-2.35 (1H, m), 2.01-2.15 (2H, m), 1.19-1.38 (2H, m), 1.13 (1H, ddd, J=10.51, 6.85, 5.14 Hz), 0.89-1.00 (1H, m)

Specific rotatory power: (α)D20, 1% in H$_2$O=18.3°

Example 5

Preparation of the Lithium Salt of (R)-4-(1-(1-(4-(trifluoromethyl) benzyl) pyrrolidin-2-carboxamide) cyclopropyl) benzoic acid 1.4 g (33.1 mmol) of lithium hydroxide monohydrate were added to a solution of 8 g (18 mmol) of methyl (R)-4-(1-(1-(4-(trifluoromethyl) benzyl) pyrrolidin-2-carboxamide) cyclopropyl) benzoate dissolved in a mixture of 50% H$_2$O-dioxane. The solution was left under stirring for 6 hours and then the dioxane was evaporated under vacuum; the residue was loaded onto a Biotage C-18 column eluting first with only water (2 column volumes) and finally with MeOH (3 column volumes). The fractions containing MeOH were concentrated and the resulting solid was dried at 60° C. under vacuum to obtain 6.9 g of Compound 1 lithium salt, (yield 88%).

$C_{23}H_{22}F_3N_2LiO_3$
MS: (ES/+) m/z: 433
$^1$H NMR (400 MHz, METHANOL-d4) δ ppm 7.88-7.83 (m, 2H), 7.66-7.62 (m, 2H), 7.60-7.55 (m, 2H), 7.16-7.10 (m, 2H), 3.87-3.72 (m, 2H), 3.18 (dd, J=4.4, 9.8 Hz, 2H), 2.55-2.44 (m, 1H), 2.32-2.20 (m, 1H), 1.89 (br s, 3H), 1.35-1.25 (m, 1H), 1.22-1.15 (m, 1H), 1.11-1.04 (m, 1H), 0.99-0.90 (m, 1H)

Example 6 Preparation of the reference compound, i.e. sodium salt of (S)-4-(1-(1-(4-(trifluoromethyl)benzyl)pyrrolidin-2-carboxamide) cyclopropyl) benzoic acid. (Compound 2)

Compound 2 was prepared according to the first process of the invention, therefore following the entire process described in example 1 comprising quantities and reagents, but starting this time from (tert-butoxycarbonyl)-L-proline instead of (tert-butoxycarbonyl)-D-Proline.

$C_{23}H_{22}F_3N_2NaO_3$.
MS: (ES/+) m/z: 433
$^1$H NMR (400 MHz, DMSO-d6) δ=8.38 (s, 1H), 7.75-7.66 (m, 4H), 7.64-7.56 (m, 2H), 6.96 (d, J=8.8 Hz, 2H), 3.86 (d, J=13.2 Hz, 1H), 3.63 (d, J=13.2 Hz, 1H), 3.13-3.07 (m, 1H), 3.03-2.96 (m, 1H), 2.40-2.31 (m, 1H), 2.19-2.05 (m, 1H), 1.87-1.69 (m, 3H), 1.21-1.06 (m, 2H), 1.05-0.91 (m, 2H)

Specific rotatory power: (α)D20, 1% in $H_2O$=−28.5°.

Pharmacological Evaluation

Example 7

Studies of Binding Towards the Human EP4 Receptor.

The experiments were performed in accordance with the procedure described by Abramovitz et al (Biochemica and Biophysica Acta; 1483, 285-293, 2000).

Tissue Preparation:

The cell membranes bearing the human EP4 receptor, stably expressed by HEK293 cells (Human Embryonic Kidney 293) were prepared as described below. After eliminating the culture medium (DMEM, supplemented with Glutamax I and containing 10% of foetal bovine serum and blasticidin 10 μg/ml) a wash of the cell monolayer was performed with 10 ml of hypotonic lysis buffer (TRIS-Cl 5 mM+EDTA 5 mM-pH 7.4). The cells, which grew in adherence in the above mentioned medium at 37° C. with 5% $CO_2$, were then detached from the growth container (150 $cm^2$ flask) and lysed by mechanical action, adding 20 ml of fresh lysis buffer. The lysates were stirred for 30 seconds and centrifuged at 40000×g for 22 minutes at 4° C. The final pellet was stored at −80° C. until use. At the time of the binding experiment, the membranes were thawed and re-suspended in analysis buffer (10 mM MES-KOH pH6, containing 10 mM MgCl2 and 1 mM CaCl2)) to obtain a concentration of 1 mg of proteins/ml. The protein content of the membrane suspension was determined using bovine serum albumin as a standard.

Binding Test:

In the experiments, 10 μl aliquots of membranes were incubated with the radioligand [$^3$H]-Prostaglandin E2 ($PGE_2$) at the concentration of 1 nM, in absence or in presence of various concentrations of the compounds to be tested. The non-specific binding was determined in the presence of $PGE_2$ 1 μM. The incubation, in a final volume of 0.1 ml, performed in 96 deepwell microplates, proceeded for 90 minutes at 25° C. The separation of the free radioligand from that bound to the receptor occurred by rapid filtration under vacuum, using Unifilter GFB glass fibre filtering microplates, pre-wetted with 0.3% of polyethyleneimine dissolved in the analysis buffer, followed by 3 washes with cold buffer (50 mM HEPES, NaCl 500 mM, BSA 0.1%, pH 7.4). The filtration discs were then dried at 30° C., to which 0.05 ml of Microscint-20 scintillation liquid (Perkin Elmer) was added to each and at the end the radioactivity present was measured after at least one hour of stabilization. The compound/radioligand competition curves were analysed using the "Non linear curve fitting" program (Graph Pad, version 7 for Windows), which allowed calculating the $IC_{50}$ value (concentration capable of inhibiting the 50% of the radioligand binding to the receptor under examination) for each compound evaluated.

Results: The results thus obtained are expressed as $IC_{50}$ values, and are shown in the following Table 1.

TABLE 1

Binding to the recombinant human EP4 receptor.

| Compound | [$^3$H]-$PGE_2$ binding IC50 (nM ± SD) |
|---|---|
| Compound 1 | 45.0 ± 0.4 |
| CR6086 | 48.0 ± 3.0 |
| Compound 2 | 2206 ± 940 |

From the data shown in the table it can be seen how both Compound 1 and CR6086 demonstrated a powerful activity in inhibiting the binding to the EP4 receptor; Compound 1 showed inhibitory activity towards the binding of the $PGE_2$ ligand practically identical to that obtained with the comparative compound CR6086. The inventors noted and considered it interesting that the EP4 antagonist activity of Compound 1 was stereo-specific since Compound 2, which is the reference "S form" enantiometer of Compound 1, i.e. (S)-4-(1-(1-(4-(trifluoromethyl) benzyl) pyrrolidin-2-carboxamide)cyclopropyl)benzoic acid, was about 50 times less active in inhibiting the binding of the $PGE_2$ ligand to the human EP4 receptor.

Example 8

Determination of cAMP in CHO Cells Transfected with Human EP4 Receptor (Functional Test)

Method: Evaluation of the agonist and antagonist activity of Compound 1 in the human EP4 receptor expressed in CHO cells transfected with the human EP4 receptor, determined by measuring its effects on cAMP production in the absence and in the presence of the endogenous agonist $PGE_2$.

The CHO cells were suspended in HBSS buffer (Invitrogen) with the addition of HEPES 20 mM (pH 7.4) and IBMX 500 mM, then distributed in microplates at a density of 20000 cells per well and incubated for 10 minutes at room temperature in the absence (control) or in presence of the compound under examination. As a reference control of the agonist activity, 1 μM of $PGE_2$ was added to independent dosage wells. In the case of the evaluation of the antagonistic effect, the reference agonist $PGE_2$ was instead added to a final concentration of 30 nM. After 10 minutes of incubation at room temperature, the cells were lysed and the fluorescence acceptor (cAMP labelled D2) and the fluorescence donor (anti-cAMP antibody labelled with europium cryptate) were added. After 60 minutes at room temperature, the fluorescence transfer was measured at a wavelength of 337 nm in excitation and at 620 and 665 nm in emission using a microplate reader (Envison, Perkin Elmer). The cAMP concentration was determined by dividing the measured signal at 665 nm by that measured at 620 nm (ratio). The results were expressed, in the case of the evaluation of the agonist effect, as a percentage of the control response at 1 µM of $PGE_2$ while, in the case of the evaluation of the antagonist effect, as a percentage of inhibition of the response of the control agonist at 30 nM $PGE_2$. For the determination of the antagonist activity, the apparent dissociation constant (Kb) was calculated by applying the modified Cheng Prusoff equation ($Kb=IC_{50}/(1+A/EC_{50}A)$); where A=concentration of the reference agonist $PGE_2$, and $EC_{50}A=EC_{50}$ value of the reference agonist.

Results:

The functional cAMP test showed that Compound 1 was a pure antagonist of the human EP4 receptors (Kb values: 15 nM Compound 1 versus 7.8 nM CR6086) with no agonist-type activity.

Compound 1
Agonist effect: inactive up to $10^{-6}$M
Antagonist effect: IC50=$1.6 \times 10^{-7}$ M; Kb=$1.5 \times 10^{-8}$M
CR6086
Agonist effect: inactive up to $10^{-6}$M
Antagonist effect: $IC_{50}$=$8.2 \times 10^{-8}$M; Kb=$7.8 \times 10^{-9}$ M Example 9

Ex-Vivo Functional Test: Evaluation in the Rat of EP4 Receptor Occupation by Compound 1 (30 mg/kg) Compared to CR6086 (30 mg/kg)

Method: The release of the cytokine TNF alpha induced by the endotoxin Lipopolysaccharide (from *E. coli*) and modulated by increasing concentrations of $PGE_2$ was evaluated, by the cells present in the whole blood of the rat and expressing the EP4 receptor. As it is known from the literature, $PGE_2$ modulates this release by inhibiting it, and the compounds tested, selective for the EP4 receptor, if present in the blood following their uptake, will be bound to the receptor, preventing $PGE_2$ from inhibiting cytokine release. This reversal effect of the modulation of TNF alpha release can be considered a biomarker of the antagonism towards the EP4 receptor.

Male Wistar rats (Charles River, Italy) weighing 250-275 g were used, orally treated with a vehicle or Compound 1 (30 mg/kg) or CR6086 (30 mg/kg). Each treatment group consisted of 6 animals.

Measurement of the Ex-Vivo Effects in Whole Blood of the Rat:

The effects of the receptor occupancy by the compounds under examination was evaluated one hour after their administration, and compared to those measured in the presence of the vehicle alone. After gaseous anaesthesia with isofluorane, blood was taken from the abdominal aorta and transferred to tubes containing heparin (0.1-0.2 U/ml). Then 0.4 ml blood aliquots were taken and dispensed into a series of test tubes which were pre-heated at 37° C. for 10 minutes. LPS (0.1 µg/ml final concentration) were added to the samples, which represented the test control, or an LPS mix (0.1 µg/ml final concentration)+$PGE_2$ at various concentrations. In the samples representing the basal release of cytokine, LPS was replaced by sterile phosphate buffer (PBS). The samples were incubated for 4 hours at 37° C., then 40 µl of 10 mM EDTA were added and the samples were transferred into ice. The samples were then centrifuged at 1500×g for 10 minutes at 4° C. and the plasma thus obtained was removed and stored at −80° C. until the time of the dosing. The content of TNF alpha in the plasma was measured by means of a specific commercial kit.

The final concentrations of TNF alpha were calculated for each animal treated and for each experimental condition, from which the percentage of inhibition due to increasing concentrations of $PGE_2$ were obtained, compared to the sample containing only LPS. The cytokine release baseline values resulted to be below the ELISA assay sensitivity limit, indicated by the manufacturer. Therefore, the $IC_{50}$ value was calculated from this inhibition curve. For each treatment group, $PGE_2$ inhibition curves were constructed (mean±SD of the inhibition vs $PGE_2$ concentration) as shown in FIG. 1. The mean TNF alpha values of the samples in presence of only LPS, in the different treatment groups were analysed to verify the possible intrinsic effect of the compound under examination. The results thus obtained are illustrated in FIG. 1.

As can be seen in FIG. 1, as expected, increasing concentrations of $PGE_2$ (range 10-1000 nM) inhibited the release of TNF alpha, in a concentration-dependent manner. After the treatment with CR6086 or Compound 1, statistically significant reversion of the effect of $PGE_2$ was observed (**p<0.01 vs vehicle group; two-way ANOVA), due to the presence of the selective receptor antagonist. The $IC_{50}$ value of $PGE_2$ calculated for each treatment group with the compounds is significantly higher than that calculated after treatment with the vehicle, suggesting the same $PGE_2$ power shift due to the presence of the antagonists. No differences were observed between the effects due to the two compounds and both show no significant effects per se on the release of TNF alpha (in absence of $PGE_2$).

Example 10

Collagen Arthritis in the Mouse (CIA): Effect of Compound 1 Compared with CR6086 in a Model of Rheumatoid Arthritis in the Mouse Method: Arthritis was induced in the mouse by intradermal injection of heterologous collagen emulsified in Freund's complete adjuvant (CFA). The arthritis that developed was characterized by a marked destruction of the articular cartilage with the deposit of immune complexes, synovitis and periarticular inflammation. The collagen acted as an antigen and induced an immune response that involved both T and B lymphocytes, with the production of anti-collagen antibodies. Studies carried out in the mouse with this experimental model allowed to identify many of the cytokines and chemokines involved in the pathogenesis of human rheumatoid arthritis. After gaseous anaesthesia with isoflurane/02, adult male DBA/1 mice were immunized by intradermal injection at the base of the tail with 100 µl of an emulsion containing 200 µg of type II bovine collagen in CFA. The CFA was in turn composed of 3 mg/ml of Micobacterium tuberculosis suspended in a mixture of paraffin oil and mono-oleate mannide. A group of non-immunized animals served as a healthy control group. The mice were enrolled for the study at the onset of the first clinical symptoms of the pathology, such as oedema and redness on the rear and front paws. At different times from the induction of the pathology, the degree of pathology was assessed by assigning clinical scores according to the following scale: 0=normal, 1=slight redness and swelling of the ankles, 2=pronounced oedema, 3=severe oedema and ankylosis; the clinical score values assigned to each paw were then added. The volume of the 4 paws was also measured and summed using a micro-gauge. At the end of the study, the animals were sacrificed and the 4 paws were taken, fixed in 10% formalin and processed for histological analysis. The preparations were analysed with an optical microscope to assess the degradation of cartilage and bone, inflammatory cell infiltration and synovial inflammation. For this purpose, scores were assigned to quantify the severity of the individual parameters evaluated. The drugs to be tested were considered effective if able to counteract the progression of the disease, by reducing oedema, the clinical score and tissue damage to the joints. Compound 1 (45-90 mg/kg) and CR6086 (30 mg/kg), dissolved in distilled water, were administered orally for 16 days during the progression of the pathology.

Statistical analysis. The values were expressed as group mean±standard error and analysed with GraphPad Prism software, version 6.0. The statistical analysis was carried out with the different measurements taken on day 16, 24 hours after the final treatment. The ANOVA one-way variance analysis was carried out followed by the Dunnett test for multiple comparisons for oedema values. For the analysis of clinical and histopathological score values, the sum of the scores of the 4 paws was analysed by means of the ANOVA-Kruskall-Wallis non-parametric test, followed by the Dunn test for multiple comparisons. For the statistical analyses performed, a value lower than P=0.05 was considered significant.

Figure 2:
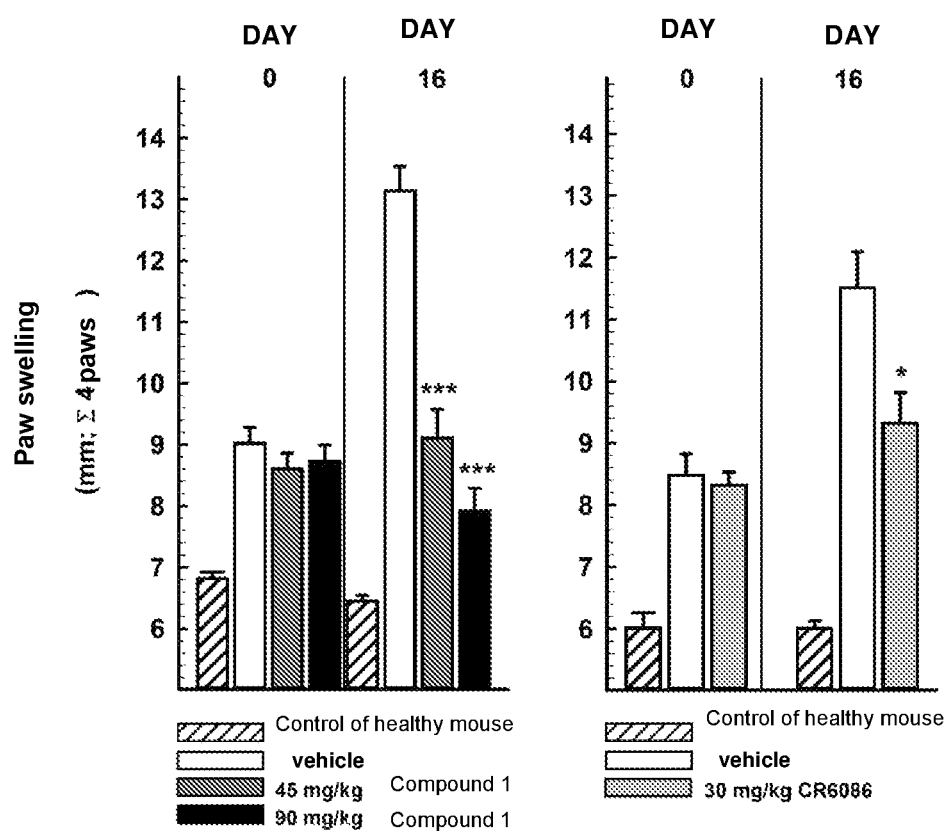
FIG. 2 shows the CIA evaluation of the oedema of example 10.
Figure 3:
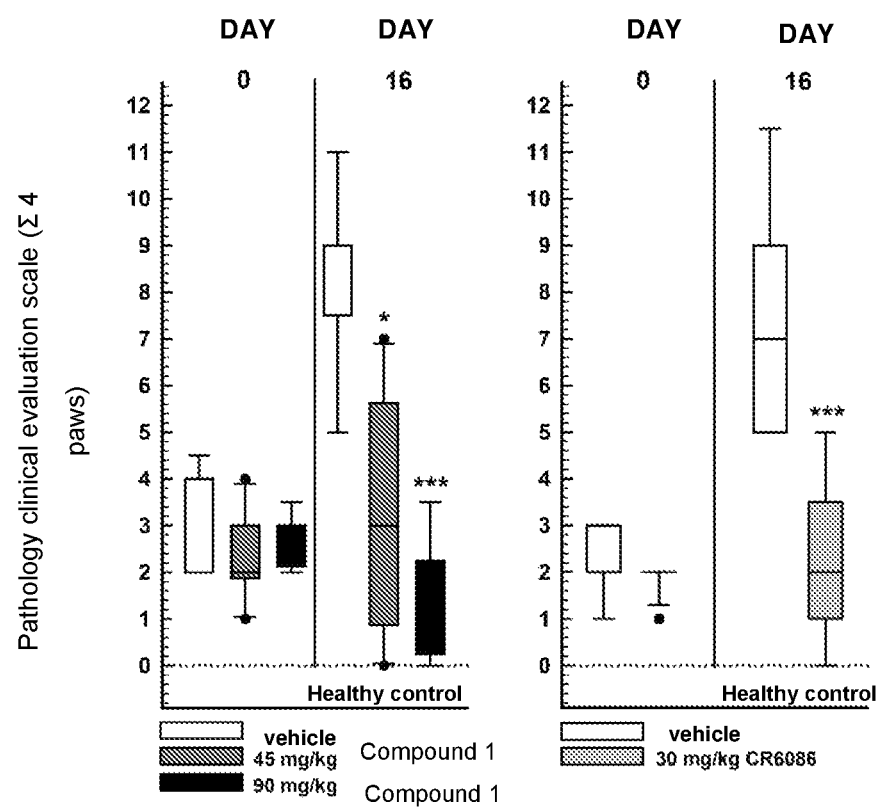
FIG. 3 shows the CIA clinical evaluation of example 10.

Results:

The therapeutic effect of compound 1 was evaluated, administered orally at doses of 45 and 90 mg/kg, on the progression of collagen-induced arthritis in mice. Compound 1 significantly and in a dose-dependent manner reduced the evolution of the pathology over the 16 days of drug treatment. The results thus obtained are summarized graphically in FIG. 2, which shows the CIA evaluation of the oedema, and in FIG. 3 which reports the CIA clinical evaluation.

This effect was present in all the parameters analysed, i.e. oedema (***P<0.001 vs vehicle; Dunnett test), clinical and histopathological score (*P<0.05, ***P<0.001 vs vehicle; Dunnett test).

Comparing the results related to oedema (FIG. 2) and clinical score (FIG. 3) with those obtained for the selective EP4 antagonist CR6086 at a dose of 30 mg/kg in a similar study, there was a greater effect on the reversion of clinical symptoms (swelling of paws) by compound 1 at a dose of 45 mg/kg. This result allows to conclude that the two compounds, at the same dose, can manifest the same powerful therapeutic activity on the progression of arthritis in the mouse.

Example 11

Pharmacokinetics

Compound 1 administered to Wistar rats demonstrated an excellent oral bioavailability. In fact, when administered at a dose of 5 mg/kg, Compound 1 exhibited a $C_{MAX}$ of 4270 ng/ml and an AUC (0-24 h) of 5460 ngxh/ml. The $C_{MAX}$ concentration of 4270 ng/ml was equivalent to a plasma concentration of about 9000 nM, concentration that is about 200 times greater than the $IC_{50}$ value obtainable from Table 1. This result fully justified the activity of Compound 1 in inhibiting inflammation (swelling of the paw) in the CIA model illustrated in FIG. 2.

The invention claimed is:

1. (R)-4-(1-(1-(4-(trifluoromethyl)benzyl) pyrrodiline-2-carboxamide) cyclopropyl benzoic acid (Compound 1) having the following structure:

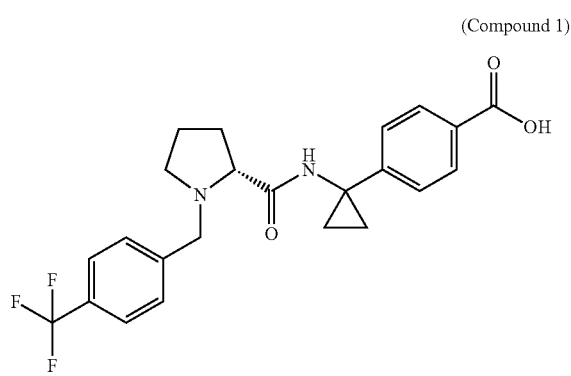 [SMILES: O=C(O)c1ccc(C2(NC(=O)[C@H]3CCCN3Cc3ccc(C(F)(F)F)cc3)CC2)cc1]

(Compound 1)

or a salt thereof.

2. The compound according to claim 1 wherein the salt is a sodium salt.

3. The compound according to claim 1 wherein the salt is a lithium salt.

4. The compound according to claim 1 wherein the salt is a hydrochloride salt.

5. A process for the preparation of (R)-4-(1-(1-(4-(trifluoromethyl)benzyl) pyrrodiline-2-carboxamide) cyclopropyl benzoic acid (Compound 1) or a salt thereof according claim 1, comprising the following steps:

a) forming the amide (intermediate P1) by reacting (tert-butoxycarbonyl)-D-proline (N-tert-butyloxycarbonyl-D-proline) with methyl 4-(1-aminocyclopropyl) in the presence of a coupling agent

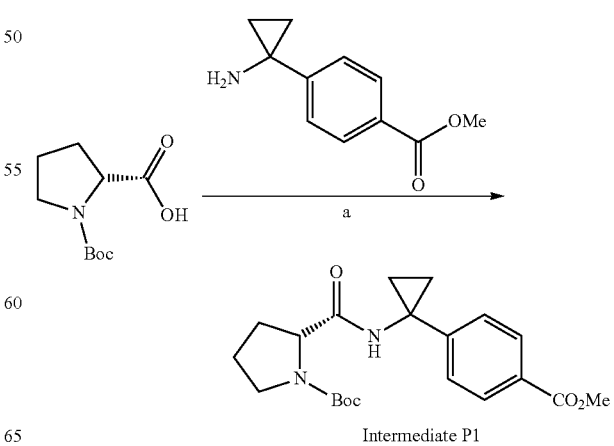

Intermediate P1 b) deprotecting the tert-butyloxycarbonyl group of the intermediate P1 with at least one acid in order to obtain the intermediate P2

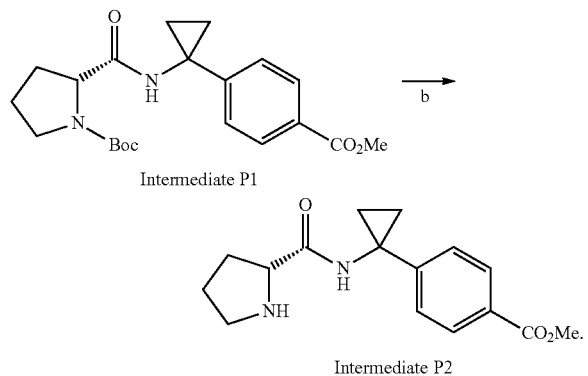

Intermediate P1

Intermediate P2 c) alkylating the intermediate P2 with 4-trifluoromethyl benzyl bromide in the presence of a base in order to obtain the intermediate P3

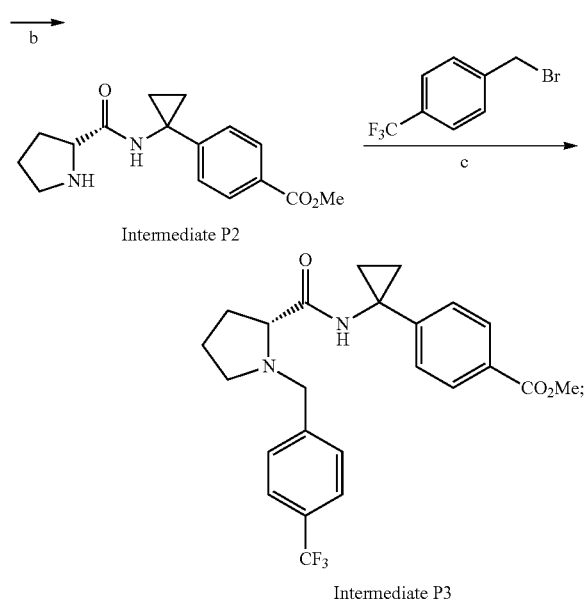

Intermediate P2

Intermediate P3 and
d) hydrolyzing the intermediate P3 in the presence of a strong base in order to obtain the Compound 1

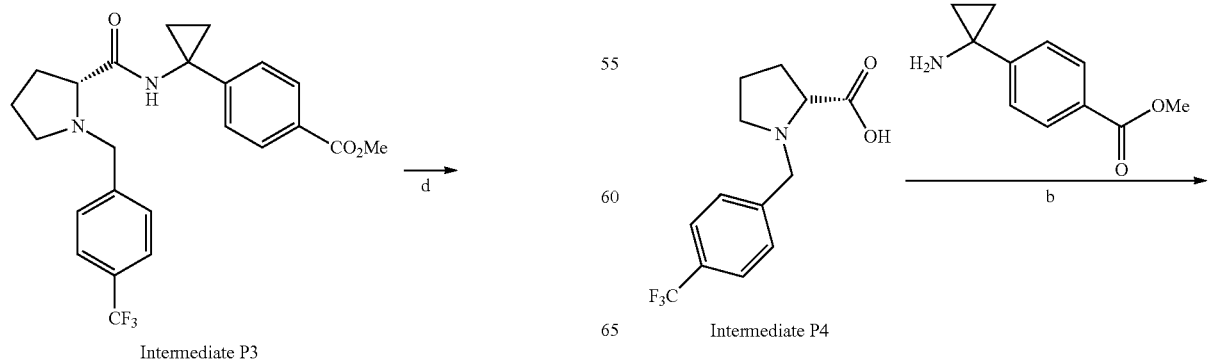

Intermediate P3

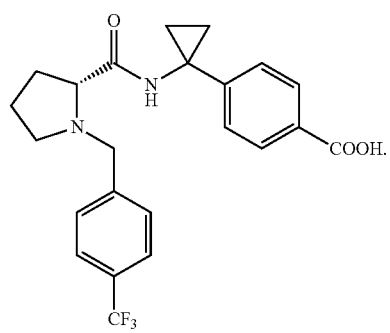

Compound 1

6. The process according to claim 5, wherein the coupling agent of step a) is 1-ethyl-3-(3-dimethylaminopropyl)carbodiimide.

7. The process according to claim 5, wherein in step b) the at least one acid is 2,2,2-trifluoroacetic acid.

8. The process according to claim 5, wherein in step c) the base is cesium carbonate.

9. The process according to claim 5, wherein in step d) the strong base is sodium hydroxide.

10. A process for the preparation of (R)-4-(1-(1-(4-(trifluoromethyl)benzyl) pyrrodiline-2-carboxamide) cyclopropyl benzoic acid (Compound 1) or a salt thereof according to claim 1, comprising the following steps:

a) alkylating D-Proline with 4-trifluoromethylbenzyl bromide in the presence of a strong base employing an alcohol as solvent in order to obtain the intermediate P4

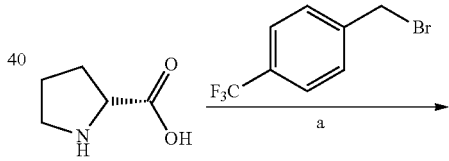

Intermediate P4 b) forming the amide (Intermediate P3) by reacting the intermediate P4 with methyl 4-(1-aminocyclopropyl) benzoate in the presence of a coupling agent

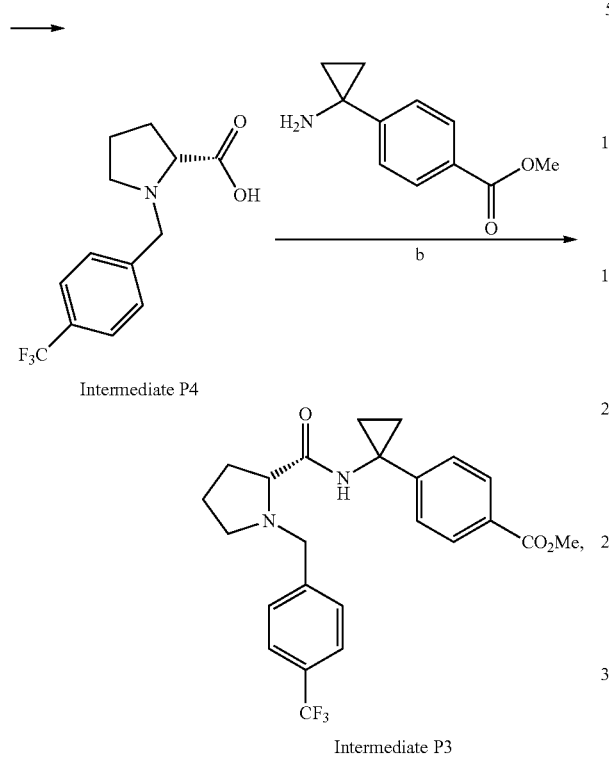

Intermediate P3 and
c) hydrolysing the Intermediate P3 in the presence of a base in order to obtain the Compound 1

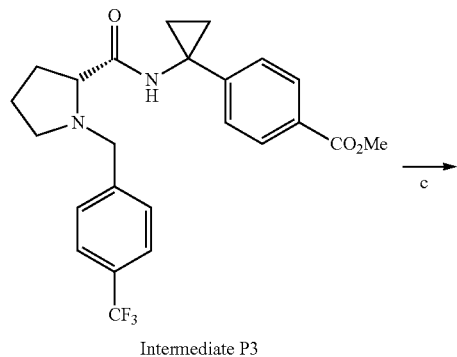

Intermediate P3

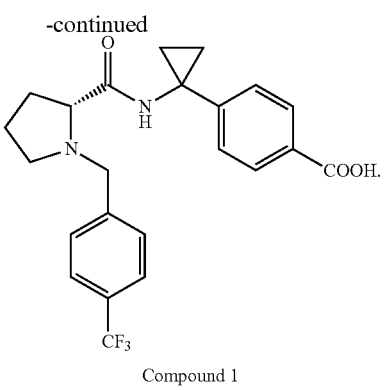

Compound 1

11. The process according to claim 10, wherein in step a) the base is potassium hydroxide and the alcohol is 2-propanol.

12. The process according to claim 10, wherein in step b) the coupling agent 1-ethyl-3-(3-dimethylaminopropyl) carbodiimide.

13. The process according to claim 10, wherein in step c) the strong base is sodium hydroxide.

14. A pharmaceutical composition comprising the compound or a pharmaceutically acceptable salt thereof according to claim 1 and pharmaceutically acceptable excipients.

15. A method for the treatment of a pathology that involves the activity of prostaglandin E2 (PGE2) in its pathogenesis, said method comprising: administering, to a subject in need thereof, (R)-4-(1-(1-(4-(trifluoromethyl)benzyl)pyrrodiline-2-carboxamide) cyclopropyl benzoic acid (Compound 1) or a pharmaceutically acceptable salt thereof according to claim 1 as an EP4 receptor antagonist in the treatment of said pathology that involves the activities of prostaglandin $E_2$ ($PGE_2$) in its pathogenesis, wherein the pathology is selected from the group consisting of rheumatoid arthritis, spondylarthritis, psoriatic arthritis and ankylosing spondylitis, arthrosis and acute and chronic pain due to inflammation, osteoarthritis pain, arthritis pain with immunologic aetiology and rheumatoid arthritis.

16. The method according to claim 15, wherein the pathology is an eye disease.

17. The method according to claim 15, wherein the pathology is endometriosis.

18. The method according to claim 15, wherein the pathology is selected from the group consisting of retinopathy of prematurity (ROP), proliferative diabetic retinopathy and age-related macular degeneration (AMD).

* * * * *